United States Patent [19]

Crossland et al.

[11] Patent Number: 5,190,904

[45] Date of Patent: Mar. 2, 1993

[54] PARAFFIN ALKYLATION CATALYST

[75] Inventors: Clifford S. Crossland, Houston, Tex.; Alan Johnson, Ontario, Canada; John Woods, Ontario, Canada; Elliot G. Pitt, Ontario, Canada

[73] Assignee: Chemical Research & Licensing Company, Pasadena, Tex.

[21] Appl. No.: 791,106

[22] Filed: Nov. 12, 1991

Related U.S. Application Data

[62] Division of Ser. No. 632,478, Dec. 24, 1990, Pat. No. 5,157,196.

[51] Int. Cl.$^5$ .................. B01J 29/04; B01J 21/08; B01J 27/06
[52] U.S. Cl. ........................ 502/85; 502/63; 502/224; 502/232; 502/246
[58] Field of Search ............... 502/224, 232, 85, 246, 502/63

[56] References Cited

U.S. PATENT DOCUMENTS

| | | | |
|---|---|---|---|
| 3,109,042 | 10/1963 | Mayer | 585/720 |
| 3,544,652 | 12/1970 | Van Dijk | 585/720 |
| 3,655,813 | 4/1972 | Kirsch et al. | 260/683.43 |
| 3,706,814 | 12/1972 | Kirsch et al. | 260/683.43 |
| 3,851,004 | 11/1974 | Yang | 260/671 |
| 3,852,371 | 12/1974 | Kemp | 260/683.47 |
| 3,879,489 | 4/1975 | Yurchak et al. | 260/683.44 |
| 3,893,942 | 7/1975 | Yang | 252/411 |
| 3,917,738 | 11/1975 | Fenske et al. | 260/683.43 |
| 3,925,251 | 12/1975 | Rodewald et al. | 502/224 |
| 3,975,299 | 8/1976 | Crathorne et al. | 502/224 |
| 3,976,714 | 8/1976 | Rodewald | 260/683.47 |
| 3,979,476 | 9/1976 | Kemp | 260/683.47 |
| 4,008,291 | 2/1977 | Zabransky et al. | 260/683.43 |
| 4,056,578 | 11/1977 | McClure et al. | 260/683.47 |
| 4,180,695 | 12/1979 | McClure | 585/730 |
| 4,547,474 | 10/1985 | Olah | 502/168 |
| 4,721,559 | 1/1988 | Olah | 208/135 |
| 4,918,255 | 4/1990 | Chou et al. | 585/331 |

FOREIGN PATENT DOCUMENTS 389237  4/1975  United Kingdom .

OTHER PUBLICATIONS

Huang, T. J., and Yurchak, S., "Isoparaffin/Olefin Alkylation over Resin/Boron Trifluoride Catalysts", Symposium on Recent Advances in Alkylation presented before the Division of Petroleum Chemistry, Inc. American Chemical Society, New Orleans Meeting, Mar. 20-25, 1977, pp. 359-367.

Albright, Lyle F., "Mechanism for Alkylation of Isobutane with Light Olefins", Ibid. pp. 391-397.

Primary Examiner—Anthony McFarlane
Assistant Examiner—Nhat D. Phan
Attorney, Agent, or Firm—Kenneth H. Johnson

[57] ABSTRACT

Paraffin alkylation using solid, particulate catalyst is carried out by preparing an alkane-catalyst mixture in a wash zone, passing the alkane-catalyst mixture to a plug flow reactor where a minor amount of olefin is introduced to contact the alkane-catalyst mixture and react to form alkylate and the alkane-catalyst-alkylate mixture is passed through the reactor with a minimum of back mixing to restrict the reaction of alkylate with olefin, thus substantially preventing polymerization. The alkane-catalyst-alkylate mixture, substantially free of olefin is passed to a disengaging zone where the liquid is removed and the solid particulate catalyst is recovered and returned to the wash zone for recycle. The alkane is present in the reactor in sufficient molar excess to react substantially all of the olefin. Any unreacted isoalkane is recycled to the reactor with make-up isoalkane added to maintain the molar excess. The preferred catalyst is an acid washed silica treated with antimony pentafluoride and more preferably treated with alkane at low temperature, e.g. −30° to −160° C.

21 Claims, 1 Drawing Sheet

PARAFFIN ALKYLATION CATALYST

This is a division of application Ser. No. 07/632,478, filed Dec. 24, 1990 now U.S. Pat. No. 5,157,196.

BACKGROUND OF THE INVENTION

1. Field of the Invention

This invention relates to the alkylation of isoparaffins with olefins to yield hydrocarbons of enhanced octane number, the apparatus, catalyst and the method of preparing the catalyst.

2. Related Art

Isooctanes or trimethylpentanes (TMP) are among the most desirable components of motor alkylate gasoline and 2,2,4-trimethylpentane (isooctane) has long been the standard of measurement for the anti-knock properties of gasoline. The most common method of producing motor alkylate isooctane in commercial refineries is the alkylation of isobutane with butenes in the presence of a strong acid catalyst. Two acids currently used in alkylation plants are concentrated sulfuric acid and hydrofluoric acid. In these common processes the reactants are admixed with the acid in a contactor and the products separated from any unreacted reactants and the acid. The prior art in this area is well known. The drawbacks to the use of the sulfuric or hydrofluoric acid processes are readily apparent. Large quantities of the acids, which are highly corrosive, dangerous to handle and potentially a hazard to the environment, are required.

The search for safer particulate solid catalysts has been intense. Zeolites have been the most widely studied of the solid alkylation catalysts. For example, Kirsch, et al in U.S. Pat. Nos. 3,665,813 and 3,706,814 disclose the use of such zeolites in "continuous" alkylation processes. European Patent 0174863 discloses sulfated zirconia as a solid superacid for paraffin isomerization and isoparaffin alkylation. U.S. Pat. Nos. 4,056,578 and 4,180,695 disclose perfluoropolymersulfonic acid (PFPSA) as an alkylation catalyst U K. patent 1,389,237 discloses an antimony pentafluoride/acid on a carbon support as catalyst for alkylation. Other catalyst compositions which have been found to be initially active for alkylation include supported HF-antimony pentafluoride, (U.S. Pat. No. 3,852,371); a Lewis Acid and Group VIII metal intercalated in graphite, (U.S. Pat. No. 3,976,714); and a cation exchange resin complexed with $BF_3$ and HF (U.S. Pat. No. 3,879,489). U.S. Pat. No. 4,918,255 describes a process for alkylating isoalkanes with olefins using a Lewis acid such as boron trifluoride, boron trichloride, antimony pentafluoride or aluminum trichloride deposited on inorganic oxide such as a wide pore zeolite, $SiO_2$ or $Al_2O_3$.

Early work by Kirsch, et al, cited above using zeolites disclosed a catalyst life of about 10 grams of alkylate per gram of catalyst used. Further a method for increasing the life of zeolite catalysts using a regenerative process disclosed as in U.S. Pat. Nos. 3,851,004 and 3,893,942 issued to Chang-Lee Yang, which disclose incorporating a Group VIII metal hydrogenation agent into the catalyst composition and regenerating the partially deactivated catalyst by periodic hydrogenation. A similar catalyst was used by Zabransky, et al, in a simulated moving bed reactor as disclosed in U.S. Pat. No. 4,008,291.

Fenske et al. in U.S. Pat. No. 3,917,738 claims both oxidative and reductive regeneration techniques for zeolite catalysts. As described in this patent the olefins are adsorbed by the catalyst. A mixture of catalyst, isoalkane and olefin flows concurrently through an adsorption zone before the reactants and catalyst are introduced into the reaction zone. The controlled olefin adsorption was thought to prevent polymerization and improve catalyst life although this benefit was not quantified.

It is an advantage of the process of the present invention that the catalyst life is extended over that described in the art for solid paraffin alkylation catalysts. It is a feature of the present invention that the catalyst environment is controlled in a circulating bed reactor. It is a further feature of the present invention that the catalyst contact with olefin rich streams is minimized and contact with isoalkane is maximized. It is a further advantage of the present invention that back-mixing of the flow stream is limited. A further feature of the present invention is a catalyst which has the appropriate alkylation activity and fluidization properties for use in this process. These and other advantages and features will be seen in the following description.

SUMMARY OF THE INVENTION

This invention describes an alkylation process for producing high octane gasoline using a solid catalyst in a circulating solids reactor comprising a plugflow short contact time reaction zone, a solids disengaging zone, and a catalyst wash zone. An isoalkane-catalyst slurry is intimately mixed with an olefin rich stream at the inlet to the reaction zone then the mixture is rapidly moved through the reactor with a minimum of back mixing (to minimize secondary reactions and polymer formation). The reactor exits into a disengaging zone where the catalyst is separated from a major portion of the reactor effluent liquid. The catalyst and any associated residual alkylate then pass into a fluidized wash zone where the catalyst is washed with isoalkane to remove the residual alkylate. The isoalkane-catalyst slurry is then returned to the reactor. The reaction is preferably at least partially in the liquid phase. Suitable isoalkanes have 4–7 carbon atoms and suitable olefins include $C_2$ to $C_5$ olefins, e.g., ethylene, propylene, butenes, and pentenes or mixtures thereof.

The process may be used with any suitable solid catalyst having the appropriate alkylation activity and fluidization properties.

In addition, the rapid removal of catalyst from the reaction zone in a flowing liquid stream prevents excessive temperature excursions.

In another aspect the present invention relates to a catalyst for paraffin alkylations. Briefly the catalyst is an acid washed silica treated with antimony pentafluoride and preferably activated at low temperature with an alkane or isoalkane.

Another aspect of the present invention is the reactor in which the reaction is carried out.

DETAILED DESCRIPTION OF THE PREFERRED EMBODIMENT

The scope of the present invention is not limited by any particular hypothetical mechanism. Isoalkanes comprise isobutane, isopentane, isohexanes and isoheptanes. The olefin comprises ethylene, propylene, butenes and pentenes Mixtures of the various reactants within the ranges are not only contemplated, but are the usual condition in commercial streams.

Figure 1:
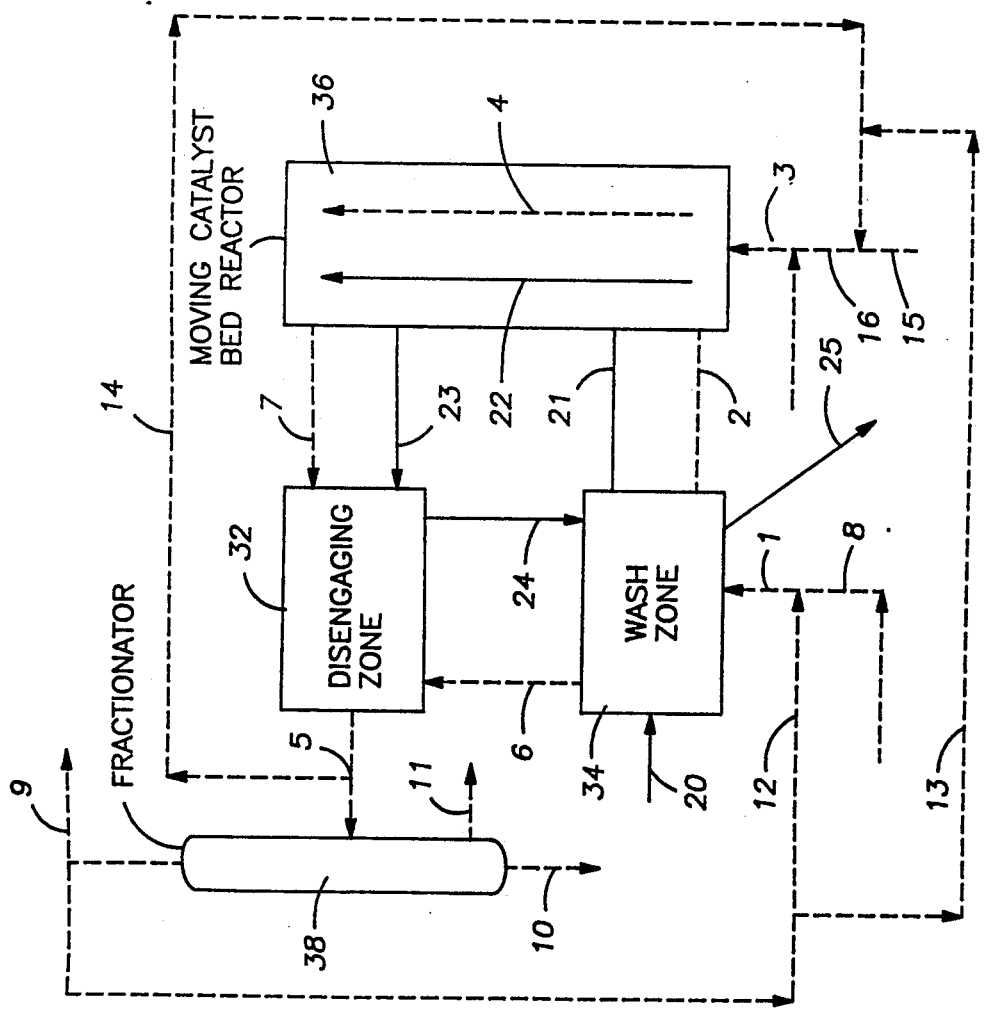
FIG. 1 is a schematic representation of an upflow slurry reactor embodiment of the present invention.

In schematic FIG. 1 the three operational elements of the system as shown as reaction zone 36, disengaging zone 32 and wash zone 34. In practice these could be different zones of a single vessel with appropriate piping, screens and the like.

The liquid flow is depicted by the dashed lines 1, 2, 3, 4, 5, 6, 7, 8, 9, 10, 11, 12, 13, 14, 15 and 16 and the solid (catalyst) flow is depicted by the solid lines 20, 21, 22, 23, 24 and 25. The alkylation of isobutane with butenes is used to illustrate the invention.

The role of the isobutane wash is to prepare the catalyst for the alkylation reaction. In the present invention this preparation step may be carried out in the catalyst wash zone by purging the catalyst with isobutane prior to returning the catalyst to the reaction zone. In this wash zone the hydride transfer reaction as thought to occur:

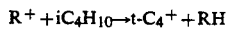

Thus the catalyst wash zone serves a number of purposes including:

(a) increasing the proportion of t-butylcarbocations (t-$C_4^+$) at the catalyst active sites (b) surrounding the active sites with isobutane rich fluid in the intraparticle and interparticle void space. To do this the reacted catalyst 23 is separated from the reactor effluent liquid 7 in the disengaging zone 32. As it is transported as stream 24 to the wash zone 34 it is washed in a countercurrent manner by the isobutane rich fluid stream 6 from the wash zone. The wash zone is typically operated as a fluid bed to provide efficient washing of the catalyst. When operating a fluid bed, the liquid superficial velocity can range from the minimum catalyst fluidization velocity to the catalyst free fall velocity. It is normally preferred to operate the wash zone above the minimum fluidization velocity and below the catalyst free fall velocity.

The residence time of the catalyst in the wash zone may be varied from about 5 seconds to about 1 hour but is preferably between 30 sec. and 5 minutes. It is desirable to minimize the wash time consistent with achieving the stated aims of the wash zone function.

The wash zone can be operated over a broad range of temperatures, for example, from −50° C. to +100° C., preferably within the range −40° C. to +50° C. The pressure in the wash zone may be extended over a wide range, for example, from atmospheric pressure to 1000 psig, but should always be sufficient to maintain the wash hydrocarbon as a liquid.

The wash fluid is typically a combination of the isobutane rich recycle stream 12 recovered from fractionation plus any make-up isobutane (stream 8) required to balance the consumption of isobutane in the reactor and any losses from the process.

Catalyst may be added (stream 20) and withdrawn (stream 25) from the wash zone both to control the catalyst inventory and the catalytic activity. The washed catalyst (stream 21) plus a portion of the associated wash fluid (stream 2) are withdrawn as a slurry from wash zone 34 and transferred to the reaction zone 36 where the slurry contacts and reacts with the olefin feed (stream 3). At the inlet to the reaction zone, the ratio of isobutane to olefin may be varied from about 2 to 1 to about 1000 to 1, preferably from 5 to 500 to 1.

The desired ratio may be achieved by adding an isobutane rich stream to dilute the olefin feed stream 16 (either stream 13 or stream 14) prior to mixing with the catalyst slurry. The isobutane diluent for the olefin stream may be obtained directly from a portion of stream 5 (via stream 14) or stream 9 (via stream 13) or any mixture of these two streams. An external source of diluent (stream 15) may also be used either alone or in admixture with the above streams.

The catalyst slurry (streams 21/2) is uniformly dispersed into the feed stream 3 with the catalyst addition being controlled to provide sufficient active sites to react with all the olefin and maximize the production of trimethylpentanes. The amount of solid catalyst added will be dependent on the nature of the catalyst and reactor design but typically would be in the range from 1:100 to 1:1 volume of catalyst to volume of total liquid in the reactor and from 5:1 to 15:1 volume of catalyst to volume of olefin in the reactor. The reacting slurry (streams 2/4) is rapidly transported through the reaction zone with a minimum of back mixing to the disengaging zone 32.

Typical residence times in the reaction zone are from about 1 second to about 5 minutes or preferably from about 1 sec to 30 sec. The reactor can be operated over a broad range of temperatures, for example, from −50° C. to 100° C., preferably within the range −40° C. to +50° C. The pressure in the reaction vessel may be extended over a wide range, for example, from atmospheric pressure to 1000 psig, but should be sufficient to maintain at least a major portion of the hydrocarbon in the liquid phase. Within the scope of the invention a number of possible reactor configurations are envisaged, including an upflow reactor, a downflow reactor and a horizontal flow reactor. The movement of the reacting slurry through the reaction zone with the minimum of back mixing may be achieved by selecting the appropriate flow rates or by the use of mechanical devices such as an auger or a progressive cavity pump.

The disengaging zone 32 may be based on any device that rapidly separates the slurry (streams 23/7) into liquid stream 5 free of solids and a falling solid stream 24. Such devices include cyclones, or the like The catalyst is immediately subjected to washing by the isobutane rich stream 6 as it is returned to the wash vessel. The reactor liquid effluent is fractionated in vessel 38 to yield alkylate products, stream 10, a sidedraw stream Il, an isobutane rich overhead stream 9. The temperature and pressure of the disengaging zone would typically be that of the reactor.

The process may be used with any suitable solid alkylation catalyst having the appropriate alkylation activity and fluidization properties. A number of catalysts and supports were tested and found useful for the present process and apparatus. A preferred catalyst comprises acid washed silica treated with antimony pentafluoride.

The silica is preferably a material having a surface area of about 5 m$^2$/g to about 250 m$^2$/g; pore volume of about 0.1 cc/g to about 4.0 cc/g; bulk density of 9–100 pounds/cu ft. and particle size distribution in the range of 35–240 microns which has been acid washed, water washed and dried prior to treatment with antimony pentafluoride.

The acid wash preferably comprises a strong inorganic acid such as HCl, $H_2SO_4$ or $H_3PO_4$, however, relatively strong organic acids may be employed. The acid wash is conducted by contacting the support with an excess of acid from about 5 minutes to 16 hours or longer. After the acid is removed, the solid catalyst is washed with water to substantially remove the residual acid and dried for few minutes to several hours at 80° to 150° C. then heated to between 160° and 650° C. for several hours The support may be prepared in an inert, reducing or oxidizing atmosphere Antimony pentafluoride as a liquid, a solution in an appropriate solvent, such as $SO_2$ or $SO_2ClF$, or as a vapor is contacted with the acid washed silica. The amount of antimony pentafluoride incorporated in the silica is from about 5 to 80% of the weight of the total of support and antimony pentafluoride.

This catalyst is preferably activated by treating it with an alkane (the term is used here to include both normal or isoalkanes) having 3 to 7 carbon atoms at a temperature in the range of −30° C. to −160° C. for a sufficient time to improve the activity of the catalyst over that of the untreated catalyst.

A number of catalysts and supports were screened and found to be useful for the present process and apparatus, however it has been found that a silica support treated with $SbF_5$ produces an active catalyst with the required fluidization properties which produces alkylate at or in excess of present commercial sulphuric acid catalyst.

TYPICAL CATALYST PREPARATION

The following is a typical preparation of the preferred silica/$SbF_5$ catalyst.

Typical Silica properties

United Catalyst Silica L3573
Surface Area 185 $m^2/g$
Bulk Density 16.3 lb/cu. ft.
pH 6.3
LOI (1000° C.) 5 wt %

Preparation of Acid Washed Silica 250 g of silica were added to 1.5 L of 1 N HCl with occasional stirring. The mixture was allowed to sit for 16 hours before filtering off the acid. The silica was washed with deionized water until the washings were neutral. The silica was heated in an oven at 90° C. for 2 hours then at 120° C. for 2 hours, finally at 220° C. for 2 hours.

The silica was then sieved and the 140-200 mesh (106-75 μ) material was stored in an oven at 220° C.

Preparation of Catalyst for Example 1

A sample of 140-200 mesh silica was removed from the oven and stored in a desiccator until cool. 0.61 g of silica was then transferred to a 30 cc Teflon vial. The silica was kept under dry nitrogen in a Glove Box as liquid $SbF_5$ (0.86 g) was added. The vial was capped and shaken for 20 minutes. The resulting free flowing catalyst was used in Examples 1 to 3.

The following three examples illustrate the benefits of the present invention over a fixed bed operation with and without recycle.

EXAMPLE 1

COMPARATIVE-FIXED BED

A solid silica (75–106 μ) treated with antimony pentafluoride (as described above in the catalyst preparation) was packed into a ¼" tubular reactor, which was cooled to −80° C. then charged with isobutane. The temperature was increased to 10° C. and a mixture of isobutane and butene-2 was charged to the reactor. The initial operating conditions are shown in Table I.

TABLE I

| Fixed Bed Alkylation Initial Operating Conditions | |
|---|---|
| Catalyst, wt. g | 1.39 |
| $SbF_5/SiO_2$ Ratio, w/w | 1.4 |
| i-Butane Flow, ml/h | 102 |
| Butene-2 Flow, ml/h | 3.5 |
| Pressure, psig | 150 |
| Temperature, °C. | −10 |
| $iC_4$/olefin wt. ratio | 30.2 |

The alkylation reaction was monitored by analyzing snap samples of the reactor effluent stream at 90 minute intervals using an on-line capillary gas chromatograph fitted with an automatic sample injection valve. After this the reactor effluent was partially vaporized across a back pressure regulator to produce an isobutane rich gas stream and an alkylate liquid. The liquid was collected in a receiver at ambient conditions. The receiver was periodically drained and the liquid weighed. The flow of the isobutane rich vapor was continuously measured using a wet test meter. The on-line analysis determines the concentration of all the major components in the reactor effluent from propane to 2,2,5-trimethylhexane as well as the remaining $C_{9+}$ components by carbon number. A summary of the analytical data along with data calculated from the analyses is presented in Table II. These include the research and motor octane numbers (RON and MON), the alkylate yield in terms of g of alkylate/g olefin charged, and the isobutane/olefin weight ratio. During the run the reactor temperature was raised to compensate for a decrease in catalyst activity. These changes together with the hours on-stream are also recorded in Table II. These data show that this catalyst is active for alkylation, although the quality of the alkylate is poor. The total weight of alkylate collected before catalyst deactivation was 18.9 g which corresponds to 23.3 g of alkylate/g $SbF_5$.

TABLE II

| Fixed Bed Reactor Alkylation Results | | | | | |
|---|---|---|---|---|---|
| Run No.: 347 | | | | | |
| HRS ON-LINE | 1.5 | 2.5 | 4.0 | 5.5 | 7.0 |
| REACT. TEMP. C. | −10 | −10 | −10 | 0 | 0 |
| REACTOR EFFLUENT WT. % ANALYSIS | | | | | |
| C3 | 0.08 | 0.08 | 0.08 | 0.08 | 0.08 |
| iC4 | 92.32 | 92.95 | 93.25 | 93.35 | 94.71 |
| nC4 | 0.46 | 0.43 | 0.46 | 0.46 | 0.45 |
| trans C4− | 0.00 | 0.00 | 0.00 | 0.00 | 0.10 |
| cis C4− | 0.00 | 0.00 | 0.00 | 0.00 | 0.02 |
| C5+ ALKYLATE | 7.14 | 6.55 | 6.21 | 6.12 | 4.65 |
| PRODUCT PROFILE WT. % | | | | | |
| TMP | 26.7 | 35.1 | 42.4 | 43.3 | 44.9 |
| DMH | 23.7 | 17.8 | 13.4 | 12.5 | 5.9 |
| C5-C7 | 28.1 | 22.0 | 15.8 | 14.2 | 8.1 |
| C9-C11 | 14.3 | 13.2 | 11.7 | 10.9 | 8.8 |
| C12 | 4.3 | 7.4 | 9.7 | 10.9 | 17.2 |
| C13+ | 2.9 | 4.5 | 7.0 | 8.2 | 15.2 |
| RON | 86.0 | 89.5 | 91.5 | 91.8 | 95.4 |
| MON | 85.6 | 88.5 | 90.3 | 90.6 | 93.3 |
| ALKYLATE g/g | 2.1 | 2.0 | 2.0 | 1.9 | 1.8 |

EXAMPLE 2

COMPARATIVE

For this experiment, the fixed bed reactor of Example 1 was modified to return a portion of the effluent from the reactor outlet to the reactor inlet thus allowing operation as a recycle reactor. A further batch of alkylation catalyst of Example 1 was charged to the tubular reactor. Isobutane at $-80°$ C. was charged to the (cooled) reactor then the temperature was increased to 10° C. An alkylation experiment was carried out with the initial conditions given in Table III.

TABLE III

Recycle Reactor Alkylation
Initial Operating Conditions

| | |
|---|---|
| Catalyst, wt., g | 1.37 |
| $SbF_5/SiO_2$ Ratio, w/w | 1.63 |
| i-Butane Flow, ml/h | 200 |
| Butene-2 Flow, ml/h | 5 |
| Recycle Flow, ml/min | 20 |
| Pressure, psig | 125 |
| Temperature, °C. | $-10$ |
| $iC_4$/Olefin, wt. ratio | 36.7 |

The experiment was monitored in a similar manner to Example 1 and the results for this experiment are summarized in Table IV.

TABLE IV

Recycle Reactor Alkylation Results
Run No.: 309

| HRS ON-LINE | 2 | 5 | 8 | 11 | 14 | 17 |
|---|---|---|---|---|---|---|
| REACT. TEMP. C. | $-10$ | $-10$ | $-10$ | 0 | 0 | 0 |
| REACTOR EFFLUENT WT. % ANALYSIS | | | | | | |
| C3 | 0.16 | 0.15 | 0.15 | 0.15 | 0.15 | 0.15 |
| iC4 | 93.82 | 94.11 | 94.29 | 94.37 | 94.59 | 96.85 |
| nC4 | 0.38 | 0.33 | 0.33 | 0.33 | 0.31 | 0.31 |
| trans C4— | 0.00 | 0.00 | 0.00 | 0.00 | 0.00 | 0.37 |
| cis C4— | 0.00 | 0.00 | 0.00 | 0.00 | 0.00 | 0.26 |
| C5+ ALKYLATE | | | | | | |
| PRODUCT PROFILE WT. % | | | | | | |
| TMP | 43.7 | 57.5 | 62.5 | 63.8 | 68.6 | 50.9 |
| DMH | 21.3 | 11.2 | 6.5 | 5.7 | 4.9 | 3.7 |
| C5-C7 | 21.9 | 14.9 | 10.4 | 10.5 | 10.9 | 9.3 |
| C9-C11 | 9.0 | 7.9 | 7.1 | 6.8 | 5.8 | 12.1 |
| C12 | 3.9 | 8.0 | 12.3 | 11.8 | 9.1 | 21.1 |
| C13+ | 0.2 | 0.6 | 1.3 | 1.5 | 0.7 | 2.9 |
| RON | 89.0 | 93.9 | 96.4 | 96.7 | 97.4 | 96.6 |
| MON | 88.4 | 92.5 | 94.4 | 94.5 | 95.0 | 93.9 |
| ALKYLATE g/g | 2.1 | 2.1 | 2.0 | 2.0 | 2.0 | 1.9 |

As can be seen from the product profile there is an increase in the TMP concentration with on-stream line time but there is also a proportionally greater increase in the $C_{12+}$ material concentration. To compensate for this the reactor temperature was increased after 11 hours on-stream. This caused a temporary decrease in the $C_{12+}$ concentration but eventually this heavy alkylate concentration started to increase and the catalyst was deactivated.

The amount of alkylate collected from this fixed bed recycle run was 78.5 g which corresponds to 92.4 g/g $SbF_5$. In comparing the results from Example 2 with that of Example 1 there is a significant improvement by using recycle.

EXAMPLE 3

Figure 2:
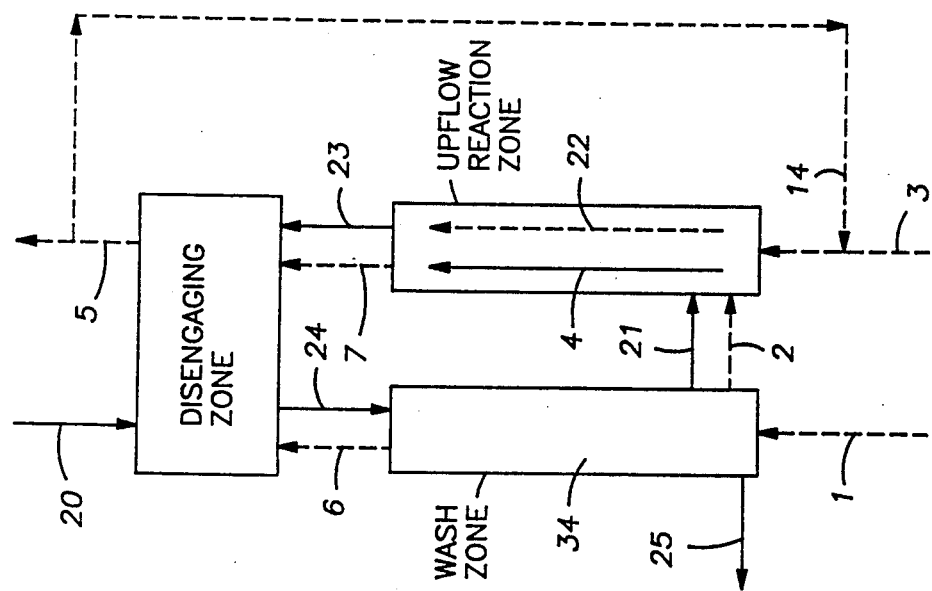
FIG. 2 is a schematic representation of an alternative reactor embodiment of FIG. 1.

This example was carried out using a circulating bed reactor according to the present invention. FIG. 2 shows the essentials of this upflow reactor unit In this unit a portion of the reactor effluent is recycled to provide sufficient flow to transport the catalyst through the reactor. Initially the unit was filled with isobutane, then the catalyst as described in Example 1 after treatment with isobutane at $-80°$ C. was added via the disengaging zone 32 to the wash zone 34. The catalyst bed in the wash zone was fluidized with cooled isobutane wash fluid (stream 1) then the cooled recycle flow (stream 14) was adjusted to transport catalyst through the reactor to the disengaging zone thus establishing the appropriate catalyst circulation (streams 22 21, 22, 23 and 24) before the butene-2 feed, stream 3, was introduced to the unit via the recycle stream 14.

Table V gives the initial operating conditions while VI records the progress of the alkylation experiment.

TABLE V

Circulating Bed Alkylation
Initial Operating Conditions

| | |
|---|---|
| Catalyst, wt. g | 1.54 |
| $SbF_5/SiO_2$ Ratio, w/w | 1.52 |
| i-Butane Wash Flow, ml/h | 105 |
| Butene-2 Flow, ml/h | 3.3 |
| Recycle Flow, ml/min | 21.5 |
| Pressure, psig | 150 |
| Reactor Inlet Temp., °C. | $-15$ |
| Disengager Outlet Temp., °C. | 4.8 |
| $iC_4$/Olefin Wt. Ratio | 29.2 |
| Liq. Residence Time in Reactor, sec. | $\approx 2.4$ |
| Cat. Residence Time in Reactor, sec. | $\approx 3.2$ |
| Cat. Residence Time in Wash Zone, sec. | $\approx 40$ |

By comparing these results (Table IV) with those obtained from Example 2 (Table IV) it can be seen that the initial alkylate quality is much improved. There is a much higher proportion of TMP and much less $C_{12}$ plus material, cracked products ($C_5$ to $C_7$ and $C_9$ to $C_{11}$) and isomerized products (DMH). This improvement is attributed to the nature of the circulating bed operation where the catalyst is continually rejuvenated by washing with isobutane then the isobutane rich catalyst is rapidly moved through the olefin reaction zone to allow TMP production but limit the production of other alkylate. As the alkylation reaction proceeds (Table VI) there is only a minor change in alkylate quality with on-stream time, with the $C_{12+}$ concentration being relatively constant for the initial 140 hours of operation.

TABLE VI

Circulating Bed Alkylation Results
Run No.: 2050-S

| HRS ON-LINE | 1 | 7 | 20 | 26 | 44 | 72 | 96 | 108 | 140 | 164 | 188 | 208 |
|---|---|---|---|---|---|---|---|---|---|---|---|---|
| REACTOR Tin. C. | $-20$ | | $-15.0$ | | | $-14.7$ | $-15.0$ | $-14.7$ | $-14.9$ | $-7.0$ | 6.4 | |
| REACTOR Tout. C. | | | 4.8 | | | 5.0 | 4.3 | 5.2 | 6.6 | 8.0 | 14.0 | |
| REACTOR EFFLUENT WT. % ANALYSIS | | | | | | | | | | | | |
| C3 | 0.15 | 0.01 | 0.00 | 0.00 | 0.00 | 0.00 | 0.00 | 0.00 | 0.00 | 0.00 | 0.01 | 0.00 |
| iC4 | 95.03 | 93.46 | 93.29 | 93.55 | 93.25 | 93.52 | 93.39 | 93.34 | 93.62 | 93.74 | 92.99 | 97.04 |
| nC4 | 0.36 | 0.00 | 0.00 | 0.00 | 0.00 | 0.00 | 0.00 | 0.00 | 0.00 | 0.00 | 0.00 | 0.00 |
| trans C4— | 0.00 | 0.00 | 0.00 | 0.00 | 0.00 | 0.00 | 0.00 | 0.00 | 0.00 | 0.00 | 0.00 | 0.65 |
| cis C4— | 0.00 | 0.00 | 0.00 | 0.00 | 0.00 | 0.00 | 0.00 | 0.00 | 0.00 | 0.00 | 0.00 | 0.38 |
| C5+ ALKYLATE | 4.46 | 6.53 | 6.71 | 6.45 | 6.75 | 6.48 | 6.61 | 6.66 | 6.38 | 6.26 | 6.99 | 1.93 |
| PRODUCT PROFILE WT. % | | | | | | | | | | | | |
| TMP | 73.9 | 76.7 | 79.3 | 78.5 | 79.8 | 79.3 | 80.6 | 79.4 | 77.0 | 78.6 | 73.4 | 46.1 |

TABLE VI-continued

Circulating Bed Alkylation Results
Run No.: 2050-S

| | | | | | | | | | | | | |
|---|---|---|---|---|---|---|---|---|---|---|---|---|
| DMH | 17.4 | 14.5 | 11.0 | 12.5 | 10.4 | 12.1 | 9.9 | 10.3 | 9.0 | 5.7 | 6.3 | 7.8 |
| C5-C7 | 5.2 | 5.6 | 5.3 | 5.6 | 5.4 | 5.4 | 5.4 | 5.8 | 6.5 | 5.2 | 6.7 | 10.5 |
| C9-C11 | 1.5 | 1.3 | 1.7 | 1.3 | 1.9 | 1.4 | 1.6 | 1.9 | 2.6 | 2.8 | 4.0 | 9.5 |
| C12 | 1.9 | 1.9 | 2.6 | 2.1 | 2.5 | 1.7 | 2.4 | 2.6 | 4.8 | 7.6 | 9.4 | 21.3 |
| C13+ | 0.0 | 0.0 | 0.1 | 0.0 | 0.0 | 0.0 | 0.0 | 0.0 | 0.1 | 0.1 | 0.2 | 4.8 |
| RON | 94.1 | 95.1 | 96.5 | 95.9 | 96.8 | 96.2 | 97.0 | 96.7 | 96.9 | 98.3 | 97.6 | 94.2 |
| MON | 93.1 | 93.9 | 94.9 | 94.5 | 95.1 | 94.7 | 95.4 | 95.1 | 95.2 | 96.1 | 95.3 | 92.0 |
| ALKYLATE g/g | 2.1 | 2.1 | 2.0 | 2.1 | 2.0 | 2.1 | 2.1 | 2.1 | 2.0 | 2.0 | 2.0 | 1.9 |

Product Quality Summary-Circulating Bed

| | Average | Range |
|---|---|---|
| Calculated | | |
| RON | 96.3 | 94.1–98.3 |
| MON | 94.7 | 93.1–96.1 |

This experiment was terminated after 208 hours of operation due to catalyst deactivation. 506.3 g of liquid alkylate was collected which equates to 544.4 g alkylate/g SbF$_5$.

For this run, the butene-2 feed addition was accurately measured using a calibrated burette and this measurement was used to calculate a total alkylate production of 810 g or 871 g of alkylate/g SbF$_5$ (3.5 bbl/lb). The discrepancy between the alkylate produced and collected was shown to be caused by the loss of C$_{5+}$ material in the vaporized isobutane rich gas stream.

Thus it can be seen that the circulating bed reactor gives a much better catalyst life than either the fixed bed (Example 1) or the recycle reactor (Example 2). Furthermore, Tables II, IV and VI show that the alkylate quality obtained from the circulating bed reactor is far superior to either the fixed bed or recycle reactor.

EXAMPLE 4

Downflow Operation

In one embodiment of the invention the reaction is carried out in the liquid phase with downflow through the reactor to limit back mixing. The solid particulate catalyst is slurried in the isobutane feed stream in the wash zone and the resultant slurry is pumped upward through a lift line. The slurry is then fed near the top of a downflow reactor into the feed zone. The butene containing stream is simultaneously fed to the reactor into or near the feed zone so as to contact the catalyst.

As the mixture passes through the reactor the solid catalyst is removed from further contact with the butene feed. The catalyst is then contacted with an excess of isobutane as it falls through the disengaging zone into the wash zone to facilitate alkylate removal from the catalyst surface and intraand inter- particle voids.

The separated liquid product stream is fractionated to recover the alkylate product and the excess isobutane is recycled to the mixing zone. In the wash zone make-up isobutane may be added to replace that consumed by the reaction. Additionally fresh catalyst is added as necessary to replace any deactivated during the process or lost from the process.

To simulate the downflow mode of operation 11 grams of catalyst consisting of a carbon support coated with trifluoromethane sulfonic acid (CF$_3$SO$_3$H) and antimony pentafluoride (SbF$_5$) were loaded into a bench scale reactor. Isobutane and olefin feed (6.7% butene-2 in isobutane) flows were set at 120 and 60 ml/hr respectively and the catalyst was recycled about every 5 minutes. The isobutane was injected after the reactor to "wash" the alkylate product away from the catalyst. The liquid product was sampled and analyzed at intervals. These results are compared to a fixed bed experiment using another sample of the catalyst in Table VII, below.

TABLE VII

| | Downflow Alkylates | | Fixed Bed Alkylates | |
|---|---|---|---|---|
| Component, wt % | Liquid 1 | Liquid 2 | Liquid 5 | Liquid 8 |
| TMP | 50.78 | 50.18 | 29.35 | 31.72 |
| C$_{12}$ | 14.80 | 16.56 | 19.33 | 18.35 |
| Other Alkylate | 27.59 | 24.02 | 19.41 | 28.94 |
| C$_{13}$+ | 6.83 | 9.23 | 31.91 | 21.00 |

The downflow mode of operation favors TMP production when compared to the fixed bed.

EXAMPLE 5

Upflow operation

In another embodiment the liquid phase reaction is carried out in upflow with the butene being injected into the lift line. With the bench scale "reactor" section acting as the disengagement segment and mixing zone, the lift line acted as the reactor. A four hour test was carried out operating in this mode using an identical catalyst to Example 4. The flow rates of olefin (C$_4$=) and isobutane were set as in example 3 above. As olefin feed was injected, the C$_{6+}$ level, as recorded by the product on-stream analyzer, slowly increased to approximately 2%. Although there was no flow reading for the lift fluid, it is estimated that the olefin residence in the lift line was only seconds.

In this mode of operation on the bench scale unit the alkylate was circulated through the system with the isobutane, and the isobutane wash was not expected to be very effective in removing the alkylation product from the catalyst. Therefore a build up of dimethyl hexanes was expected. Four liquid samples were collected during the test run and all samples were good quality alkylate with the last three collected containing in excess of 60% TMP components which compares well with commercial units (see Table VIII below).

A second test of the upflow mode was made using a PFPSA (perfluoropolymersulfonic acid) support (catalyst 2, Table VIII) treated with SbF$_5$ as the circulating catalyst. The addition of the SbF$_5$ increased problems in circulating the catalyst and it was not possible to achieve smooth circulation with the treated catalyst. While the initial liquid was poor quality, two later samples contained over 60% TMP components with total C$_{12+}$ of only about 10%.

TABLE VIII

| | Analysis of Upflow Liquids | | | | | | |
|---|---|---|---|---|---|---|---|
| | Catalyst 1 | | | | Catalyst 2 | | |
| Component, wt % | Liq. 1 | Liq. 2 | Liq. 3 | Liq. 4 | Liq. 2 | Liq. 5 | Rec. |
| TMP | 45.16 | 67.46 | 64.76 | 60.12 | 53.77 | 60.67 | 60.96 |
| $C_{12}$ | 9.59 | 4.00 | 6.24 | 10.77 | 8.80 | 5.16 | 5.04 |
| Other Alk. | 21.79 | 22.27 | 25.35 | 24.82 | 21.78 | 28.68 | 28.70 |
| $C_{13}^+$ | 23.46 | 6.27 | 3.65 | 4.29 | 15.65 | 5.48 | 5.29 |
| RON | 87.9 | 91.6 | 91.3 | 91.2 | 88.9 | 87.9 | 89.3 |
| MON | 87.5 | 90.3 | 89.3 | 89.9 | 87.5 | 86.7 | 88.7 |

EXAMPLE 6

Upflow With Mechanical Lift

A bench scale reactor was modified to provide a lifting screw conveyor or auger which substantially filled the inner diameter of the reactor. The auger was provided with a variable speed drive so that recirculation rates could be varied. A mixing or isobutane wash zone was provided along with a disengaging vessel so that product alkylate within the circulating liquid could be tested. Again, the alkylate product was not separated from the recirculating liquid, so a build up of dimethylhexanes could be expected if the isobutane wash was not effective.

The catalyst used was prepared by first depositing triflic acid ($CF_3SO_3H$) onto a carbon support by vapor deposition and then adding antimony pentafluoride ($SbF_5$) by vapor deposition. The final catalyst contained 12.88 g carbon, 0.69 g triflic acid and 5.73 g of antimony pentafluoride ($SbF_5$).

The reactor was purged with dry nitrogen during catalyst loading, and then pressured to 150 psig. The isobutane was introduced into the reactor to establish a liquid level with initial flow at 180 ml/hr which was reduced to a final flow of 60 ml/hr. The auger speed was set at 180 rpm and the pressure maintained at 150 psig. Olefin feed was set at 60 ml/hr. As the olefin was added the temperature increased from 21° C. to about 29° C. while the concentration of $C_{6+}$ and isopentane ($iC_5$) in the reactor effluent also increased.

The reactor effluent composition (see Liquid 1 in Table IX below) indicated significant cracking and isomerization. This was manifest in a low TMP/DMH ratio of 0.26 and significant $C_5$-$C_7$ components (11.8%). In addition there was a significant concentration of $C_{12}$ and $C_{13+}$ components (12.1% and 9.8% respectively. This was attributed to inadequate contacting in the reactor or non-optimum active sites distribution on the catalyst surface.

At this point the auger speed was increased to approximately 400 rpm to increase the catalyst circulation. The $C_{6+}$, $iC_5$, $nC_5$, and $nC_4$ concentration in the reactor effluent and the reactor temperature continued to increase (35° C.). Analysis of the resulting liquid (Liquid 2 in Table IX below) showed that isomerization and cracking activity had increased (TMP/DMH=0.17, $C_5$-$C_7$=18%) while the production of $C_{12}$ (5.4%) and $C_{13+}$ material (2.9%) had decreased.

A final test with the same catalyst loading was made to check the effect of high throughput. In addition, the reactor was placed in an ice bath to moderate cracking and isomerization reactions and improve temperature control.

The isobutane was started at 60 ml/hr and the unit flushed with isobutane. The olefin feed flow was then set at 240 ml/hr with the auger speed set at 180 rpm. The liquid recovered (Liquid 3, Table IX) contained a reasonable $C_{6+}$ to $iC_5$ concentration (12.2% and 0.4%) which suggested that the higher throughput and lower reactor temperature (0° C.) reduced cracking and isomerization. The analysis of the liquid sample showed it to be commercial alkylate quality.

TABLE IX

| | Mechanical Lift Test Runs | | |
|---|---|---|---|
| Composition, wt % | Liq. 1 | Liq. 2 | Liq. 3 |
| TMP | 12.27 | 9.27 | 63.81 |
| Trimethylhexane | 1.36 | 2.23 | 1.89 |
| $C_5$-$C_7$ | 11.80 | 18.02 | 5.95 |
| DMH + MH | 47.40 | 53.89 | 6.71 |
| $C_9$-$C_{11}$ | 5.33 | 8.22 | 2.53 |
| $C_{12}$ | 12.11 | 5.44 | 14.26 |
| $C_{13}^+$ | 9.75 | 2.93 | 4.85 |
| RON (Calculation) | 68.8 | 67.6 | 96.8 |
| MON (Calculation) | 71.6 | 70.5 | 94.4 |

EXAMPLE 7

A test run was made over a three day period to vary the reactor temperature and contact times. A new catalyst was prepared as above but had the following composition as loaded to the reactor: Carbon-11.17 g; triflic acid-0.75 g; and $SbF_5$-3.70.

Conditions and flow rates along with product analysis of the liquid products taken at various times in the run are reported in Table X, below. The conditions resulted in substantial improvement in the TMP/DMH ratios (as high as 7.15 in Liq. 10, Table X).

TABLE X

| | Mechanical Lift Test Runs | | | | | | | | | | |
|---|---|---|---|---|---|---|---|---|---|---|---|
| | Liq. 1 | Liq. 2 | Liq. 3 | Liq. 4 | Liq. 5 | Liq. 6 | Liq. 7 | Liq. 8 | Liq. 9 | Liq. 10 | Liq. 11 |
| Temp., °C. | 8.5 | 5.6 | 6.0 | 7.0 | 8.4 | 7.8 | 8.5 | 9.5 | 9.2 | 15.0 | 24.0 |
| $iC_4$, ml/Min | 60 | → | → | → | → | → | → | → | → | → | → |
| Olefin, ml/Min | 2 | → | → | → | → | → | → | → | → | → | → |
| Auger Speed, RPM | 180 | → | → | → | → | → | → | → | → | Slight Inc. | Reduced |
| Component, wt % Product Profile: | | | | | | | | | | | |
| TMP | 35.55 | 24.41 | 29.12 | 53.16 | 62.32 | 65.07 | 66.01 | 62.16 | 62.64 | 61.67 | 57.51 |
| TMH | 2.49 | 3.87 | 4.62 | 4.68 | 3.06 | 2.49 | 2.23 | 1.63 | 3.13 | 2.30 | 1.24 |
| $C_5$-$C_7$ | 6.85 | 14.40 | 6.80 | 6.78 | 4.98 | 5.34 | 3.69 | 3.26 | 2.92 | 2.68 | 3.08 |
| DMH + MH | 41.30 | 41.18 | 41.16 | 15.72 | 12.48 | 11.30 | 10.24 | 15.53 | 10.54 | 8.62 | 8.51 |
| $C_9$-$C_{11}$ | 4.20 | 5.73 | 6.87 | 7.15 | 4.89 | 3.66 | 4.06 | 2.03 | 3.31 | 3.00 | 3.08 |
| $C_{12}$ | 8.07 | 7.87 | 9.13 | 9.40 | 9.24 | 9.41 | 10.65 | 12.25 | 10.98 | 17.62 | 21.10 |

TABLE X-continued

| | Mechanical Lift Test Runs | | | | | | | | | | |
|---|---|---|---|---|---|---|---|---|---|---|---|
| | Liq. 1 | Liq. 2 | Liq. 3 | Liq. 4 | Liq. 5 | Liq. 6 | Liq. 7 | Liq. 8 | Liq. 9 | Liq. 10 | Liq. 11 |
| $C_{13}^+$ | 2.54 | 2.54 | 2.31 | 3.11 | 3.04 | 2.74 | 3.13 | 3.13 | 3.44 | 4.11 | 5.38 |
| RON $C_{12}^-$ portion | 80.2 | 78.1 | 78.9 | 91.1 | 93.9 | 94.8 | 95.6 | 93.4 | 95.4 | 96.4 | 96.2 |
| MON | 81.3 | 79.5 | 80.2 | 90.0 | 92.5 | 93.3 | 93.9 | 92.2 | 93.5 | 94.1 | 93.4 |
| TMP/DMH | .86 | .59 | .71 | 3.38 | 4.99 | 5.75 | 6.45 | 4.00 | 5.94 | 7.15 | 6.76 |

EXAMPLE 8

Using the upflow apparatus previously described the alkylation was carried out using a catalyst prepared as described in Example 1. The catalyst was transferred to the stainless steel hopper, cooled and isobutane added. The reactor was filled with isobutane and the catalyst was added from the hopper.

The catalyst was fluidized with isobutane wash and recycle and the bed height recorded for incipient circulation (see Table VII). The recycle rate was increased to give a bed dH (height differential) of 1 cm and butene-2 feed was charged to the unit. A summary of the reactor conditions are set out in TABLE XI and results in TABLE XII.

TABLE XI

| Reaction Conditions: Summary | | | |
|---|---|---|---|
| Catalyst | United Silica- 1.42 g | $SbF_5$ - 2.36 g | |
| Feed | C.P. Grade Butene-2 (butadiene not detected) | | |
| Initial Operating Conditions | | | |
| i/o Ratio | | | 40 |
| Cooling Bath, temp., °C. | | | −22 |
| Reactor Inlet, temp., °C. | | | −13 |
| Reactor Outlet, temp., °C. | | | 11 |
| Pressure, psi | | | 120 |
| $iC_4$ wash, ml/h | | | 200 |
| Olefin Feed, ml/h | | | 5 |
| Recycle Rate, ml/min | | | 15 |
| Initial Bed Ht., cm | | | 14 |
| Circulating Bed, Ht., cm | | | 13 |

| Product Yield | Total, g | g/g $SbF_5$ | bbl/lb | mole/mole $SbF_5$ |
|---|---|---|---|---|
| Alkylate Collected | 870.9 | 369.0 | 1.5 | 702 |
| Corrected For Vapor Loss | 1320.8 | 559.6 | 2.28 | 1065 |

| Product Quality | Average | Range |
|---|---|---|
| Calc. RON | 95.2 | 88.5–99.0 |
| Calc. MON | 93.7 | 88.4–96.7 |

TABLE XII

| TIME ON-STREAM, HRS. | 156 | 180 | 204 | 210 |
|---|---|---|---|---|
| COMPONENTS, WT. % | | | | |
| C3 | 0.16 | 0.16 | 0.15 | 0.15 |
| iC4 | 94.67 | 94.54 | 94.47 | 95.41 |
| nC4 | 0.34 | 0.34 | 0.34 | 0.35 |
| iC5 | 0.14 | 0.12 | 0.15 | 0.18 |
| C6–C7 | 0.19 | 0.17 | 0.26 | 0.30 |
| 2,2,4-TMP | 2.37 | 2.39 | 2.08 | 1.22 |
| 2,2+2,4+2.5DMH | 0.33 | 0.29 | 0.32 | 0.25 |
| 2,3,4-TMP | 0.63 | 0.76 | 0.82 | 0.64 |
| 2.3.3-TMP | 0.59 | 0.57 | 0.47 | 0.28 |
| OTHER DMH | 0.13 | 0.14 | 0.17 | 0.15 |
| 2,2,5-TMH | 0.07 | 0.06 | 0.08 | 0.12 |
| C9 | 0.05 | 0.05 | 0.07 | 0.13 |
| C10–C11 | 0.06 | 0.06 | 0.11 | 0.17 |
| C12 | 0.27 | 0.33 | 0.48 | 0.61 |
| C13+ | 0.01 | 0.01 | 0.02 | 0.05 |
| TOTAL (i—C5+) | 4.83 | 4.97 | 5.03 | 4.09 |
| PRODUCT PROFILE: | | | | |
| TMP | 77.79 | 78.78 | 70.34 | 54.85 |
| DMH | 5.81 | 4.99 | 6.25 | 7.18 |

TABLE XII-continued

| TIME ON-STREAM, HRS. | 156 | 180 | 204 | 210 |
|---|---|---|---|---|
| C5–C7 | 6.85 | 5.84 | 8.15 | 11.58 |
| C9–C11 | 3.74 | 3.43 | 5.26 | 10.34 |
| C12 | 5.54 | 6.70 | 9.50 | 14.87 |
| C13+ | 0.27 | 0.26 | 0.49 | 1.18 |
| RON | 97.99 | 98.47 | 97.20 | 95.28 |
| MON | 95.89 | 96.21 | 94.95 | 92.93 |
| ALKYLATE g/g cat. | 2.03 | 2.02 | 2.00 | 1.97 |
| C8: OTHER ALKY. | 5.1 | 5.2 | 3.3 | 1.6 |
| DMH/TMP | 0.07 | 0.06 | 0.09 | 0.13 |
| OLEFIN ml/h | 5.3 | 5.5 | 5.5 | 5.5 |
| RECYCLE ml/min | 30 | 27 | 30 | 30 |
| BED ht cm | 7.5 | 7.4 | 7 | 7.1 |
| INLET T. deg. C. | 0 | 0 to 2 | 5 to 21 | 21 |
| OUTLET T. deg. C. | 9 | 12 | 14 to 22 | 22 |
| C4= CHARGED | 490.4 | 570.9 | 651.4 | 671.6 |
| C4=/g $SbF_5$ | 207.8 | 241.9 | 276.0 | 284.6 |

EXAMPLE 9

CATALYST PREPARATION

As illustrated in Run (b) below acid washing of the silica significantly increases catalyst life compared to a non acid washed silica Run (a). Run (c) illustrates that the life of the acid washed silica/$SbF_5$ catalyst can be further greatly improved by initially contacting the catalyst with isobutane at a cool temperature typically between −160° C. and −30° C.

Run (a) (without acid treatment/without low temperature alkane treatment)

Silica dried at 220° C. was treated with $SbF_5$ (1 g $SiO_2$, 1.06 g $SbF_5$) by the general procedure then the mixture waas packed into a ¼" tubular reactor, which was charged with isobutane at 10° C. The alkylation activity of the catalyst was tested by charging a mixture of 6.74 wt % butene-2 in i-butane at 85 ml/h to the reactor. The equipment and procedure used to carry out the alkylation experiment is described in Example 2. No liquid alkylate was produced from this test.

Run (b) (Acid Treatment Without Low Temperature Alkane Treatment)

The silica was acid washed by contacting the silica with an excess of 1 N aqueous HCl for 16 hours then washing the silica with deionized water until the wash effluent was neutral. The alkylation experiment as described in Run (a) was repeated using the acid washed silica dried at 220 ° C. (1.02 g) treated with $SbF_5$ (1.16 g). The reactor was cooled to −22° C. during the initial isobutane purge, then the temperature was raised to 10° C. for the alkylation experiment. 40.85 g of alkylate was collected which corresponds to a catalyst life of 35.2 g alkylate/g $SbF_5$.

Run (c) (Acid Wash With Low Temperature Alkane Treatment)

The alkylation experiment described in Example (b) was repeated using acid washed silica dried at 220° C.

(1.04 g) treated with SbF$_5$ (1.05 g). The reactor was cooled to −78° C. during the initial isobutane purge then the reactor temperature was raised to −10° C. for the alkylation experiment. 209.7 g of alkylate was collected which corresponds to a catalyst life of 199.7 g alkylate/g SbF$_5$.

The invention claimed is:

1. An activated solid, particulate catalyst composition for paraffin alkylation comprising an acid washed silica which is characterized as being substantially free of acid, having been contacted with antimony pentafluoride and activated with an alkane having 3 to 7 carbon atoms at a temperature in the range of −30° to −160° C., said silica has a surface area of about 5 m$^2$/g to about 250 m$^2$/g and a pore volume of about 0.1 cc/g to about 4.0 cc/g.

2. The catalyst composition according to claim 1 wherein said silica has a particle size distribution in the range of 35-240 microns.

3. The catalyst composition according to claim 1 wherein said antimony pentafluoride comprises from 5 to 80% weight of the composition.

4. A method of preparing a solid, particulate catalyst composition for paraffin alkylation comprising:
   (a) washing particulate silica with a strong acid
   (b) separating said particulate silica and acid
   (c) washing said particulate silica with water
   (d) heating said particulate silica
   (e) contacting said particulate silica with antimony pentafluoride to produce an antimony pentafluoride containing silica and
   (f) contacting said antimony pentafluoride containing silica with C$_3$ to C$_7$ alkane at a temperature in the range of −30° C. to −160° C.

5. The method according to claim 4 wherein said strong acid is inorganic.

6. The method according to claim 5 wherein said strong acid is HCl.

7. The method according to claim 6 wherein said particulate silica is washed until neutral.

8. The method according to claim 4 wherein said heating is at a temperature in the range of 80° to 650° C.

9. The method according to claim 8 wherein said heating comprises initially heating at a temperature in the range of 80° to 150° C. for sufficient time to dry the particulate silica and thereafter heating at a temperature in the range of 160° C. to 650° C.

10. The method according to claim 4 wherein said alkane comprises isoalkane.

11. The method according to claim 10 wherein said isoalkane comprises isobutane.

12. A solid, particulate catalyst for paraffin alkylation comprising antimony pentafluoride supported on a silica base and manufactured by the steps comprising:
    (a) washing particulate silica with a strong acid
    (b) separating said particulate silica and acid
    (c) washing said particulate silica with water
    (d) heating said particulate silica
    (e) contacting said particulate silica with antimony pentafluoride to produce an antimony pentafluoride containing silica and
    (f) contacting said antimony pentafluoride containing silica with C$_3$ to C$_7$ alkane at a temperature in the range of −30° C. to −160° C.

13. The catalyst according to claim 12 wherein said silica has a surface area of about 5 m$^2$/g to about 250 m$^2$/g.

14. The catalyst according to claim 12 wherein said silica has a pore volume of about 0.1 cc/g to about 4.0 cc/g.

15. The catalyst according to claim 12 wherein said silica has a particle size distribution in the range of 35-240 microns.

16. The catalyst according to claim 12 wherein said strong acid is inorganic.

17. The catalyst according to claim 16 wherein said strong acid is HCl.

18. The catalyst according to claim 17 wherein said particulate silica is washed until neutral.

19. The catalyst according to claim 12 wherein said heating is at a temperature in the range of 80° to 650° C.

20. The catalyst according to claim 12 wherein said alkane comprises isoalkane.

21. The catalyst according to claim 20 wherein said isoalkane comprises isobutane.

* * * * *